(12) United States Patent
Mullis et al.

(10) Patent No.: US 10,756,326 B2
(45) Date of Patent: Aug. 25, 2020

(54) ELECTRICAL ENERGY SOURCE, TOOL KIT, AND METHOD FOR INSERTING AN ENERGY SOURCE INTO A TOOL

(71) Applicant: MEDARTIS HOLDING AG, Basel (CH)

(72) Inventors: Andreas Mullis, Tenniken (CH);
Hermann Zeuner, Freiburg (DE);
Jürgen Schonhardt, Rheinfelden (DE);
Micha Huber, Winterthur (CH)

(73) Assignee: MEDARTIS HOLDING AG, Basel (CH)

( * ) Notice: Subject to any disclaimer, the term of this patent is extended or adjusted under 35 U.S.C. 154(b) by 411 days.

(21) Appl. No.: 15/575,133

(22) PCT Filed: May 20, 2015

(86) PCT No.: PCT/EP2015/061053
§ 371 (c)(1),
(2) Date: Nov. 17, 2017

(87) PCT Pub. No.: WO2016/184509
PCT Pub. Date: Nov. 24, 2016

(65) Prior Publication Data
US 2018/0145306 A1    May 24, 2018

(51) Int. Cl.
*H01M 2/30* (2006.01)
*B25F 5/00* (2006.01)
(Continued)

(52) U.S. Cl.
CPC .............. *H01M 2/30* (2013.01); *A61B 17/00* (2013.01); *A61B 17/8875* (2013.01); *B25F 5/00* (2013.01);
(Continued)

(58) Field of Classification Search
CPC ....... A61B 17/00; A61B 17/8875; B25F 5/00; G08B 29/181; H01H 3/022; H01H 3/001;
(Continued)

(56) References Cited

U.S. PATENT DOCUMENTS

| 4,309,067 A | 1/1982 | Riley, Jr. |
| 6,126,670 A | 10/2000 | Walker et al. |

(Continued)

FOREIGN PATENT DOCUMENTS

| DE | 412 666 C | 4/1925 |
| DE | 2 237 279 A1 | 2/1974 |

(Continued)

OTHER PUBLICATIONS

International Search Report Corresponding to PCT/EP2015/061053 dated Feb. 22, 2016.
(Continued)

*Primary Examiner* — Miriam Stagg
*Assistant Examiner* — Lilia Nedialkova
(74) *Attorney, Agent, or Firm* — Davis & Bujold PLLC; Michael J. Bujold

(57) ABSTRACT

An electrical energy source for an electrically drivable tool containing: a main body, which extends along a longitudinal axis, having a first end and a second end lying opposite the first end with respect to the longitudinal axis; at least one first electrical terminal, which extends away from the first end and has a first diameter; and at least one second electrical terminal, which extends away from the second end and has a second diameter. A voltage is present between the first and second terminals. The first diameter is different from the second diameter. The first electrical terminal extends away from the first end, and the second electrical terminal extends away from the second end of the main body. A tool kit having at least one electrically drivable tool (Continued)

and having at least one electrical energy source and a method for inserting an energy source into an electrically drivable tool.

12 Claims, 8 Drawing Sheets

(51) Int. Cl.
*H01M 2/02* (2006.01)
*H01M 2/34* (2006.01)
*H01M 2/10* (2006.01)
*A61B 17/00* (2006.01)
*A61B 17/88* (2006.01)

(52) U.S. Cl.
CPC ......... *H01M 2/022* (2013.01); *H01M 2/1022* (2013.01); *H01M 2/34* (2013.01); *H01M 2/1055* (2013.01)

(58) Field of Classification Search
CPC .. H01H 3/002; H01H 2003/0273; H01M 2/34
See application file for complete search history.

(56) References Cited

U.S. PATENT DOCUMENTS

| | | |
|---|---|---|
| 6,257,351 B1 | 7/2001 | Ark et al. |
| 8,437,847 B2 | 5/2013 | Stump et al. |
| 8,469,540 B1* | 6/2013 | Gregory .................. F21L 4/027 362/205 |
| 2003/0077937 A1 | 4/2003 | Berg et al. |
| 2006/0117911 A1 | 6/2006 | Raines, Jr. et al. |
| 2008/0180032 A1* | 7/2008 | Kim .................... F21V 23/0421 315/151 |
| 2011/0229756 A1 | 9/2011 | Syoji |
| 2012/0071711 A1 | 3/2012 | Shelton, IV et al. |

FOREIGN PATENT DOCUMENTS

| | | |
|---|---|---|
| DE | 36 41 927 A1 | 6/1988 |
| DE | 20 2008 001 713 U1 | 6/2008 |
| DE | 10 2009 001 611 A1 | 9/2010 |
| DE | 20 2009 017 971 U1 | 12/2010 |
| EP | 1 813 200 A2 | 8/2007 |
| EP | 2 169 750 A1 | 3/2010 |
| EP | 14188180.5 | 10/2014 |
| JP | 2001338638 A | 12/2001 |
| JP | 2009176461 A | 8/2009 |
| JP | 2009301794 A | 12/2009 |

OTHER PUBLICATIONS

Written Opinion Corresponding to PCT/EP2015/061053 dated Feb. 22, 2016.
Japanese Office Action issued in corresponding Japanese Patent Application No. 2017-560147 dated May 21, 2019.

* cited by examiner

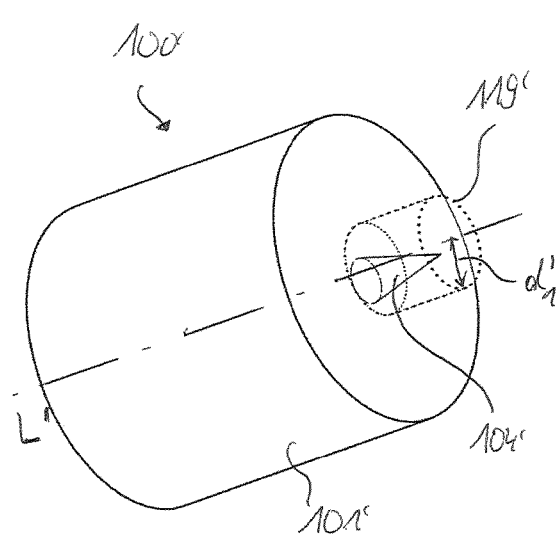
Figure 11f
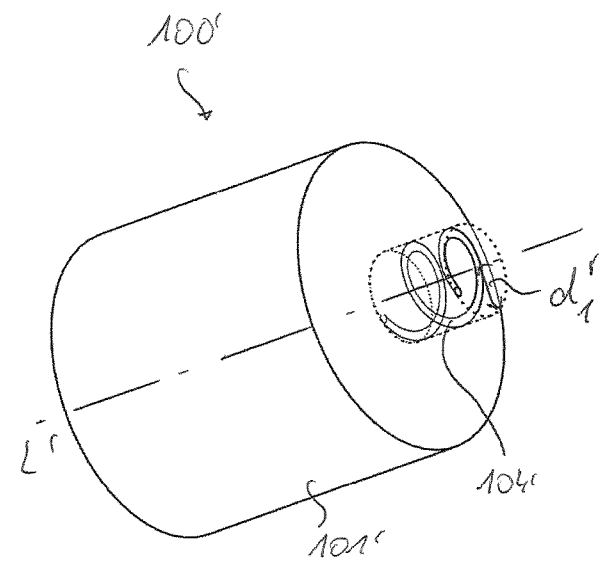
Figure 11g
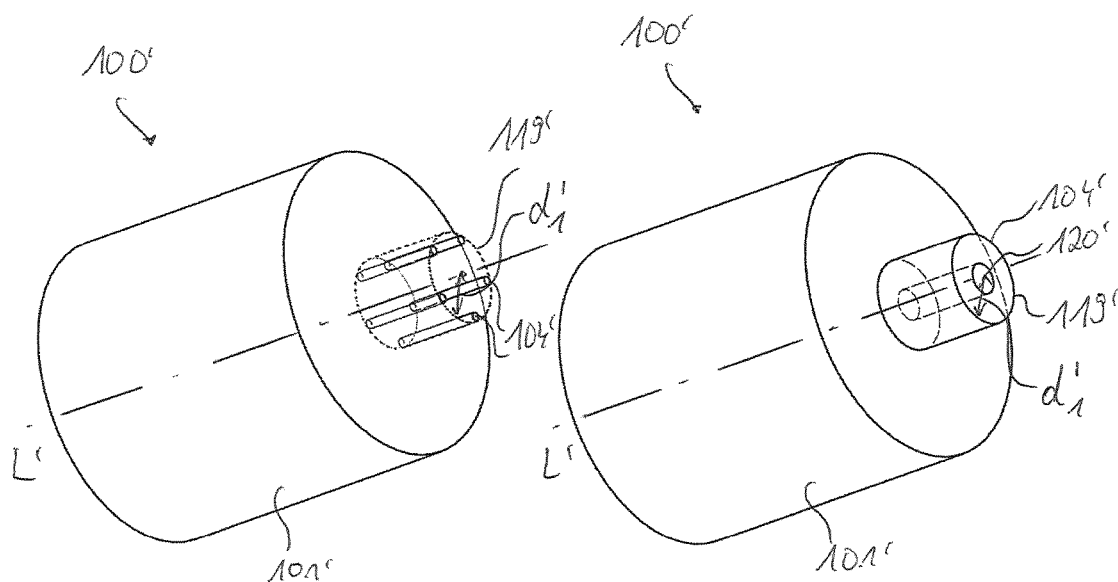
Figure 11h
Figure 11i

ELECTRICAL ENERGY SOURCE, TOOL KIT, AND METHOD FOR INSERTING AN ENERGY SOURCE INTO A TOOL

This application is a National Stage completion of PCT/EP2015/061053 filed May 20, 2015.

FIELD OF THE INVENTION

The present invention relates to electrical energy sources for electrically drivable tools, tool sets having at least one electrically drivable tool and at least one electrical energy source, and a method for inserting an energy source into an electrically drivable tool.

BACKGROUND OF THE INVENTION

In order to be driven, electrically drivable tools require an electrical energy source, which may be inserted, for example, into a cavity of the tool. The tool may be an electrically drivable surgical tool such as, for instance, a surgical screwdriver. An exemplary surgical screwdriver having a receptacle for a battery or other electrical energy source is disclosed in the European patent application EP 14188180.5.

Since the energy source is generally a direct-current source, it is important that the energy source is correctly inserted and the electrical terminals are not reversed. This is because, otherwise, the tool might become permanently damaged. Such a polarity reversal protection is also required by the standard EN 60601. Measures for preventing polarity reversal per se are already known from the prior art:

DE 4 12 666 C describes terminal connections for batteries. These have main bodies and, extending therefrom, terminal contacts that are realized as tube stubs. These tube stubs of the positive and negative terminals may differ in diameter size. The tube stubs are arranged at one and the same end of the battery. Owing to this arrangement of the terminals, however, the batteries must be of a comparatively large width perpendicularly to their longitudinal axis. The cavity of the tool, and accordingly also the tool, must thus be dimensioned accordingly; so that the battery can be accommodated. In many cases this is disadvantageous, however, for example if the tool is a surgical, screwdriver that is intended to be held in one hand. Moreover, a series connection of a plurality of batteries is rendered considerably more difficult by this arrangement of the terminals.

According to DE 2 237 279 A1, a reliable change operation is to be achieved in that the two battery terminals are realized as mutually superimposed studs having differing diameter sizes. Here also, however, the space requirement, perpendicular to the longitudinal axis of the battery is comparatively large, and here also series connection of a plurality of batteries is rendered considerably more difficult.

Furthermore, DE 10 2009 001 611 A1; discloses a battery compartment for an external cardiac pacemaker. In one exemplary embodiment, a 9-volt block, having two battery terminals of differing diameter, is used. Here, the space requirement perpendicular to the longitudinal axis of the battery is likewise comparatively large, and series connection of a plurality of batteries is rendered considerably more difficult.

DE 36 41 927 A1 relates to a polarity reversal protection for tubular batteries. For this purpose, a stepped offset is provided, which projects into receptacles of the battery holder. The batteries themselves comprise only a single terminal, extending therefrom. In many cases, however, this allows only an inadequate polarity reversal protection, since only the dimensions of this one terminal (i.e., for example, the diameter and axial length thereof) can determine whether the battery can be inserted in two opposite orientations.

A further important requirement that arises particularly in the case of surgical tools is that of preventing the reuse of the energy source. To enable the tool to be sterilized after an operation, the energy source must first be removed from the tool, since otherwise it could be destroyed as a result of the aggressive sterilization conditions, for example in that it could leak, as a result of which the sterilizer could also become contaminated. Usual energy sources can easily be inserted into the tool for a second time following sterilization. In this way, the tool could be used with an already used, and therefore at least partly discharged, energy source. This risk exists, in particular, if it cannot be seen from the outside of the energy source whether it has already been used in a tool. If this is not noticed until during the next operation, this might result in delays and consequently also in detrimental consequences for the patient. This is because, in particular, there may be an intraoperative failure of the tool. In order that the "essential power features" according to the already mentioned standard EN 60601 can also be achieved, it is necessary to prevent the reuse of the energy source.

U.S. 2006/0117911 A1 discloses battery-operated surgical screwdrivers that are intended to be used once. However, special structural measures that prevent reuse of the battery are not disclosed.

U.S. Pat. No. 6,126,670 relates to disposable battery packs that can be connected to a surgical tool in order to drive the latter. The correct polarity is achieved by means of a stud that is arranged on the tool and that engages in a corresponding opening in the battery pack. This measure, however, is not effective in preventing the battery pack from being reused.

DE 20 2000 017 971 U1 relates to handles for surgical instruments. Arranged in the handle there is an accumulator battery, which can be removed from the handle following removal of a cover. However, this document also does not disclose any mechanism that prevents reinsertion of the accumulator battery. On the contrary, it is even stated that the accumulator can be reinserted in the cavity after the latter has been sterilized.

U.S. Pat. No. 4,309,067 has as subject-matter interfaces for mechanically and electrically connecting a battery pack to a tool, which are intended to enable the battery pack to be removed, insofar as possible, with one hand. This connection is effected by means of a closure that can be actuated via a release button, which extends through a slot. However, this document also does not disclose any mechanism that prevents the battery pack from being reinserted.

The document U.S. Pat. No. 6,257,351 likewise discloses a battery pack that can be releasably connected to a surgical instrument. Here also, however, there is no disclosure of any mechanism that prevents reinsertion of the battery pack.

EP 1 813 200 A2 discloses surgical instruments having a removable battery. In one embodiment, the instrument comprises a primary portion and a grip portion that can be releasably connected to the primary portion and that contains a battery. The grip portion has a break-off portion that, after the grip portion has been separated from the primary portion, remains on the latter, such that further assembly of the said parts is no longer possible. However, this does not prevent reuse of the battery itself.

Additionally disclosed is a further exemplary embodiment of an instrument that has a counter and a motor look. In a first variant of this further exemplary embodiment, the counter is realized and arranged in such a manner that the motor look is activated after the battery has been removed from the instrument a predefined number of times (for example twice). A second variant provides that the motor look is activated after the grip portion has been separated from the primary portion a predefined number of times (for example twice). Both variants, however, are structurally complex and also susceptible to faults.

SUMMARY OF THE INVENTION

It is therefore an object of the present invention to provide an electrical energy source for an electrically drivable tool, by means of which at least one of the disadvantages of the prior art, described above, can be overcome. In particular, in at least some embodiments, the energy source is to have a least possible structural size in a direction perpendicular to a main body of the energy source, without the necessity of dispensing with the polarity reversal protection known per se in the prior art. Furthermore, in particular, at least in some embodiments, reuse of an energy source already previously inserted in a tool is to be prevented, in a manner that is as structurally simple as possible.

At least some of these objects are achieved, in a first aspect of the invention, by an electrical energy source for an electrically drivable tool. The tool may be, in particular, an electrically drivable surgical tool such as, for instance, an electrically drivable surgical screwdriver. The energy source comprises a main body, which extends along a longitudinal axis, having a first end and a second end that is opposite the first end with respect to the longitudinal axis, at least one first electrical terminal having a first diameter, and at least one second electrical terminal having a second diameter.

In this case, an electrical voltage is applied between the first terminal and the second terminal, or such an electrical voltage can be applied between these two terminals. The first diameter differs from the second diameter, in particular, the first diameter may be less than the second diameter.

Here and in the following a "diameter" of a terminal is understood to mean twice the maximum distance of all points of this terminal from the longitudinal axis of the main body. In other words, the diameter of the terminal is the least internal diameter of a notional hollow cylinder having a circular-cylindrical cavity, the longitudinal axis of which coincides with the longitudinal axis of the main body, and in which the terminal can be accommodated in its entirety.

In the structurally simplest design, one or both of the terminals may be designed in the form of a circular cylinder, wherein the longitudinal axes of these circular cylinders may be parallel to the longitudinal axis of the main body, or may even coincide therewith. Alternatively, however, one or both terminals may also be arranged eccentrically with respect to the longitudinal axis of the main body, and/or be realized, for example, in the form of a cone or a truncated cone; in connection therewith, reference is made to the exemplary embodiments to be described in detail, further below.

According to the invention, the first electrical terminal extends away from the first, end of the main body, and the second electrical terminal extends away from the second end of the main body.

If the electrically drivable tool is realized in a correspondingly suitable manner, polarity reversal can be prevented, as is also explained in greater detail further below. Since the two terminals extend away from opposite ends of the main body, a very small structural size of the energy source is rendered possible in a direction perpendicular to the longitudinal axis of the main body. In this wavy the energy source can be inserted, for example, into an electrical screwdriver of a comparatively small diameter. Furthermore, since the terminals are arranged at opposite ends of the main body, a plurality of energy sources can be connected more easily in series. Moreover, since, according to the invention, two terminals extend away from the main body and they differ in their diameter, additional dimensions are obtained, in comparison with energy sources having only one single terminal extending away from; the main body (thus, for example, two diameters and two axial lengths), that can determine whether the energy source can be inserted in two opposite orientations. The energy source can thus be protected even more reliably against polarity reversal, in that said dimensions are matched to the corresponding dimensions of the tool.

The diameter of the energy source may be in the range of from 3 mm to 50 mm. Like the definition above, the diameter of the energy source is understood to mean, twice the maximum distance of all points of the energy source from the longitudinal axis of the main body. That is to say, apart from energy sources having a cylindrical cross section, also conceivable and included in the invention, for example, are those having a square or rectangular cross section. Further, the ratio of the diameter of the first terminal and/or of the second terminal to the diameter of the energy source may be greater than 50%. In the case of a pre-defined diameter of the energy source (which may be limited, for example, by the dimensions of the tool), the diameter of the first and/or second terminal may thus be selected so as to be comparatively large, in order to produce a greater electrical contact surface. In the case of both terminals being arranged at one and the same end of the main body, as in the prior art, the contact surface would be smaller. Conversely, the ratio of the diameter of the first terminal and/or of the second terminal to the diameter of the energy source may be less than 50%.

The ratio of the first diameter of the first terminal to the second diameter of the second terminal may be in the range of from 1% to 99%, preferably from 70% to 96%, particularly preferably from 80% to 36%. The first diameter of the first terminal may be in the range of from 1 mm to 49 mm, preferably from 2 mm to 3 mm, particularly preferably from 2.4 mm to 2.6 mm. The second diameter of the second terminal may be in the range of from 1 mm to 49 mm preferably from 2.5 mm to 3.5 mm, particularly preferably from 2.5 mm to 3.1 mm. The first and/or the second terminal may be of a length, along the longitudinal axis of the main body, in the range of from 0.05 mm to 20 mm, preferably from 0.1 mm to 1 mm, particularly preferably from 0.15 mm to 0.25 mm.

In some embodiments, the first and/or the second terminal may be rigidly connected to the main body. It is also conceivable, however, and is within the scope of the invention, that at least one of the terminals is spring-mounted with respect to the main body, or is realized as a spring. This can make it easier to insert the energy source into the tool and provide for a (in particular additional) clamping action, ensuring secure mechanical, and therefore electrical, contact between the terminals of the energy source and tap-off elements of the tool.

Preferably, the main body is realized substantially in the form of a circular cylinder. This has the advantage that the energy source can be accommodated by the tool irrespective of its rotation position about the longitudinal axis—at least when the two terminals and the two tap-off elements to be brought into contact therewith also allow this.

Further of the above objects may be achieved by an electrical energy source for an electrically drivable tool that comprises:

a housing that in particular, at least partly, forms a main body as described above, in particular the outside of the main body;
   at least one voltage source, arranged in the housing, for generating an electrical voltage;
   at least one second terminal, in particular a second terminal as described above;
   at least one inner electrical contact,
      wherein the voltage generated by the voltage source is applied or can be applied between the second terminal and the inner electrical contact. The energy source may comprise one or more voltage sources, which may be connected in parallel or in series.

According to an aspect according to the invention, the energy source comprises an electrical contact element, having a first electrical contact and a second electrical contact that are electrically connected to each other, wherein
the contact element comprises a first terminal, which comprises the second contact;
the contact element is in a standby position, in which it is releasably connected, directly or indirectly, to the housing, and in which neither the first contact nor the second, contact is electrically connected to the inner contact;
by action of a force that oar; be exerted by a first tap-off element of the tool, the contact element can be moved from the standby position into an operating position in which the first contact is electrically connected to the inner contact, such that the voltage generated by the voltage source is applied between the second terminal and the first tap-off element;
after the first tap-off element has been removed for the first time, the contact element moves from the operating position into an end position in which the contact element can no longer be brought into electrical contact with the first tap-off element, such that the voltage generated by the voltage source can no longer be applied between the second terminal and the first tap-off element.

The contact element may be formed, in particular, as one place and of an electrically conductive material such as, for example, of brass, in particular of gold-plated or nickel-plated brass.

Thus, in the initial standby position, the contact element is releasably connected to the housing. For example, in the standby position, it may be clamped in, adhesive-bonded in, pressed in or welded in on the housing, or connected to the housing via at least one predetermined breaking point. In this standby position, neither the first contact nor the second contact of the contact element is electrically connected to the inner contact. Consequently, there is also no voltage applied between the contacts of the contact element and the second terminal of the energy source.

By action of a force that can be exerted by the first tap-off element, the contact, element can be moved from the standby position into the operating position. There, the first contact is electrically connected to the inner contact. In this way, the voltage generated by the voltage source is applied between the second terminal and the first tap-off element, if in this case the second terminal is also in contact with a second tap-off element of the tool, then this voltage is applied between the two tap-off elements, such that the electrical tool can be driven.

After the first tap-off element has been removed for the first, time, the contact element moves from the operating position into the end position. The force for this movement may be generated, for example, by gravity or by a spring. In the end position the contact element is no longer readily in electrical, contact with the first tap-off element. Consequently, the voltage generated by the voltage source can also no longer be applied between the second terminal and the first tap-off element. In other words, after the first tap-off element has been removed for the first time, the contact element can no longer readily be moved into a position in which the energy source is again fit to drive the tool. The reuse of the energy source is thus precluded in an effective manner, in particular the reuse of an already used, and therefore at least partly discharged, energy source. Moreover, in many exemplary embodiments, owing to the changed position of the contact element, it can be seen from the outside of the energy source that it has already been used in a tool.

In particular if the contact element is pressed in, in the standby position, on the housing, the contact element may have a holding surface, and the housing may have a counter-holding surface, wherein the contact element can be held in the standby position by mechanical contact of the holding surface with the counter-holding surface. As an alternative to this, however, it is also possible for the contact element to be held in the standby position on the housing by magnetic forces.

It is conceivable and within the scope of the invention that not only the first terminal, but also the second terminal of the energy source is part of an electrical contact element as described above. More precisely, the energy source may have a second inner electrical contact and a second electrical contact element, having a first electrical contact and a second electrical contact that are connected to each other, wherein
the second contact element comprises the second terminal, which comprises the second contact;
the second contact element is in a standby position, in which it is releasably connected, directly or indirectly, to the housing, and in which neither the first contact nor the second contact of the second contact element is electrically connected to the second inner contact;
by action of a force that can be exerted by a second tap-off element of the tool, the second contact element can be moved from the standby position into an operating position in which the first contact of the second contact element is electrically connected to the second inner contact, such that the voltage generated by the voltage source is applied between the first terminal and the second tap-off element;
after the second tap-off element has been removed for the first time, the second contact element moves from the operating position into an end position in which the second contact element can no longer be brought into electrical contact with the second tap-off element, such that the voltage generated by the voltage source can no longer be applied between the first terminal and the second tap-off element.

The contact element may have a holding body, on which the holding surface is arranged. This holding body may be realized substantially in the form, of a circular cylinder, and have a holding surface that is substantially in the form of a circumferential surface of a circular cylinder. The counter-holding surface may likewise be realized substantially in the form of a circular cylinder, other forms clearly being conceivable and within the scope of the invention. This makes it possible, during the production of the energy source, for the contact element to be connected to the housing irrespective of the rotational position about the cylinder axis, in order to obtain the initial standby position.

Advantageously, the holding body, at least in the standby position, is located on the side of the contact element that faces toward the inner contact, and the first terminal, at least in the standby position, is located on the side of the contact element that faces away from the inner contact.

The holding body of the contact element may have a holding-body diameter that is greater than the first diameter of the first terminal. As a result, the contact element can be held on the housing only by mechanical contact between the contact element and the housing, but not by mechanical contact between the first terminal and the housing.

The contact element may be movable, along a longitudinal axis of the holding surface, from the standby position into the operating position. The longitudinal axis may be, for example, an axis of symmetry of the holding surface. Preferably, the longitudinal axis of the holding surface coincides with the longitudinal axis of the main body of the energy source. In this way, the contact element can be moved particularly easily from the standby position into the operating position when the first tap-off element of the tool exerts a force thereon.

The first contact of the contact element may be realized on a cover surface of the first terminal, in particular on a cover surface of a first terminal realized in the form of a circular cylinder. In this way, an electrical contact can be made in a quite particularly simple manner between the first terminal and the first tap-off element of the tool.

The energy source, and in particular its contact element, may be realized in such a manner that the contact element, in the operating position, is clamped-in between the inner contact and the first tap-off element. In particular, this clamping may be effected in the direction of the longitudinal axis of the main body. The clamping-in can prevent the contact element from slipping in the operating position.

The energy source preferably comprises at least one cavity, in which the contact element is loosely arranged in the end position. This loose arrangement of the contact element in the end position has the effect that the contact element can slip within the cavity, in particular in a plane perpendicular to the longitudinal axis of the housing. The contact element can thus no longer readily be transferred into the operating position, in which the first tap-off element can be brought into electrical contact with the first contact of the contact element.

In order to effect this loose arrangement, it is advantageous if the cavity has an extent, along the longitudinal axis, that is greater than the height of the holding body of the contact element measured along the longitudinal axis of the main body.

It is likewise preferred for this purpose if the cavity has a cavity diameter, perpendicular to the longitudinal axis of the main body, that is greater than the holding-body diameter. Here also, the diameter of the cavity is understood in a manner analogous to the above definition. The cavity may be realized so as to be substantially in the form of a circular cylinder, the axis of symmetry coinciding with the longitudinal axis of the main body.

Alternatively or additionally, the return of the contact element to the operating position, after the first tap-off element has been removed for the first time, may also be prevented in that the contact element is held away from the operating position by further forces. This may be achieved, for example, by means of at least one magnet and/or by means of at least one spring.

The tool may have a cavity for accommodating the energy source. Advantageously, the first tap-off element is arranged on the inner side of the tool. This cover in this case is designed to hold the energy source inside the said cavity, and optionally also to close the latter. This design allows that, as a result of the cover being put on, both the first tap-off element exerts a force upon the contact element, in order to move the latter from the standby position into the operating position, and the energy source as a whole is held within the cavity, and optionally the cavity is closed, such that a reliable mechanical, and therefore electrical, contact is also made to the second terminal.

A further aspect of the present invention relates to a tool set. This tool set comprises at least one electrically drivable tool, in particular at least one electrically drivable surgical tool, in particular at least one electrically drivable surgical screwdriver, at least one electrical energy source as described above, by means of which the tool is electrically drivable.

In particular, the tool may have a first tap-off element, which is realized and arranged in such a manner that the contact element of the energy source can be moved, from the standby position into the operating position by action of a force that can be exerted by the first tap-off element. As has already been explained above, the tool may have a cavity for accommodating the energy source. Moreover, the first tap-off element may be arranged on the inner side of a cover of the tool, this cover being designed, to hold the energy source inside the cavity, optionally for closing this cavity.

If the energy source has two electrical terminals having differing diameters, and these terminals extend away from opposite ends of a main body of the energy source, then the tool preferably has a first tap-off element and a second tap-off element for tapping off the voltage that is applied or can be applied between the first terminal and the second terminal. In this case, the energy source and the tool are realized and matched to each other in such a manner that simultaneously, the first electrical terminal can be brought into contact with the first tap-off element and the second electrical terminal can be brought into contact with the second tap-off element, and the first electrical terminal cannot be brought into contact with the second tap-off element and/or the second electrical terminal cannot be brought into contact with the first tap-off element.

Consequently, the voltage that is applied or can be applied between the two terminals of the energy source can be delivered to the two tap-off elements only in one single polarity; a reversed polarity is not possible.

In order to effect this, the tool, in particular a cover of the tool, may have a first electrical insulator that encompasses the first tap-off element in the manner of a ring and projects over it in the longitudinal direction of the tool. There is thus produced a partly delimited first cavity, which is delimited by an inner wall of the first insulator and the first tap-off element. The first cavity is dimensioned such that only the first terminal of the energy source can be accommodated in the first cavity and brought into contact with the first tap-off element, but not also the second terminal. In particular, the first cavity may have a first depth, measured in the longitudinal direction of the tool, that is less than the first height of the first terminal, but greater than the first height of the second terminal. Alternatively or additionally, the first cavity may have an internal diameter that is greater than the first diameter of the first terminal, but less than the second diameter of the second terminal.

In addition, the second tap-off element preferably comprises an annular second tap-off surface, which may face toward the cavity of the tool. The second tap-off element may encompass a second insulator in the manner of a ring, and project over it in the longitudinal direction of the tool. In this way, a second cavity can be formed, which is delimited by an inner wall of the second tap-off element and the second insulator. The internal diameter of the second tap-off surface is preferably less than the second diameter of the second terminal of the energy source, but greater than the first diameter of the first terminal of the energy source. As a result of this, only the second terminal can be brought into contact with the second tap-off element. The first, terminal, by contrast, penetrates into the second cavity without being able to come into contact with the second tap-off element. For the reasons explained in connection with FIGS. 9 and 10, it is likewise advantageous if the internal diameter of the first, cavity is less than the internal diameter of the second tap-off surface.

More advantageously, the second depth of the second cavity, measured in the longitudinal direction of the tool, is less than the first length of the first terminal, measured along the longitudinal axis of the energy source. This is advantageous, in particular, if the energy source comprises a movable contact element, as described above, that comprises the holding body and the first terminal as a single piece and that is formed as a whole from a conductive material; and the diameter of the holding body is greater than the internal diameter of the second tap-off element. This is because the first terminal then strikes against the second insulator before the holding body can come into contact with the second tap-off surface.

Alternatively or additionally, the second part of the second cavity, measured in the longitudinal direction of the tool, may be less than the second length of the second terminal, measured along the longitudinal axis of the energy source, but greater than the first length of the first terminal, measured along the longitudinal axis of the energy source. In this case, however, the cover surface at the first end of the energy source, from which the first terminal extends away, should be realized as an insulator.

It may likewise be advantageous if the second tap-off element is arranged inside a ring insulator having an annular insulator surface in such a manner that the second tap-off surface is recessed, with respect to the insulator surface, by a distance that is less than the length of the second terminal. This is because this can prevent an energy source, having a terminal that does not, however, extend away from the main body, from being inserted in such a manner that this terminal comes into contact with the second tap-off surface. This advantage ensues even if the length of the terminal is less than said distance.

Yet a further aspect of the invention relates to a method for inserting an energy source as described above, having an electrical contact element, into an electrically drivable tool. The tool may be, again, an electrically drivable surgical tool, in particular an electrically drivable surgical screwdriver. The method comprises a step in which, by action of a force by the first tap-off element of the tool, the contact element of the energy source is moved from the standby position into the operating position. As established by the statements above, this achieves the effect that the voltage generated by the voltage source is applied between the second terminal, of the energy source and the first tap-off element, as a result of which the tool can be driven.

BRIEF DESCRIPTION OF THE DRAWINGS

The invention is described in greater detail in the following on the basis of a plurality of exemplary embodiments and drawings. There are shown therein

FIGS. 11a-i: schematic perspective views of further energy sources according to the invention.

DETAILED DESCRIPTION OF THE PREFERRED EMBODIMENTS

Figure 1:
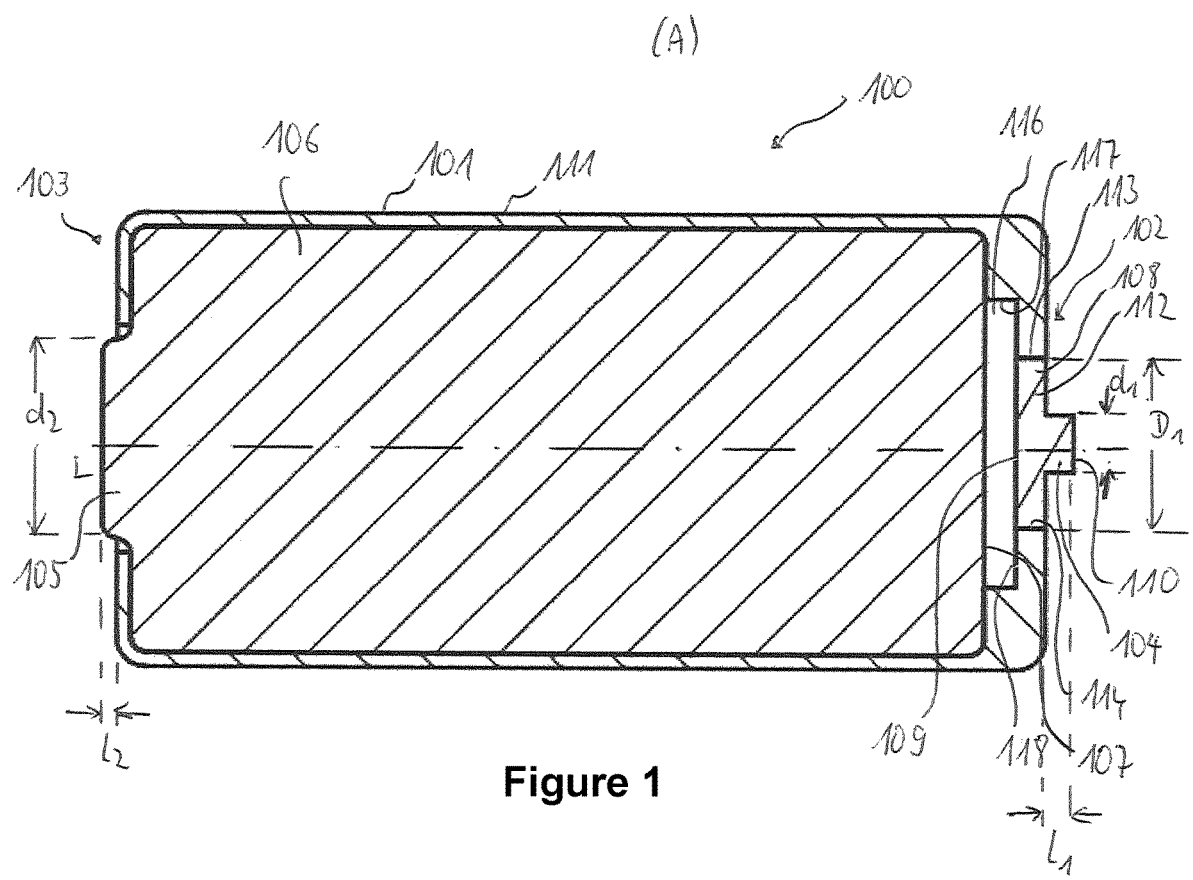
FIG. 1: a lateral sectional view of a first energy source according to the invention.

The electrical energy source 100 represented in FIG. 1 comprises a main body 101, which extends along a longitudinal axis 1. The main body 101 has a first end 102, from, which there extends away a first electrical terminal 104, and a second end 103, which is opposite the first end 102 with, respect to the longitudinal axis L and from which there extends away a second electrical terminal 105. The main body 101 has a length of 41.6 mm and a diameter of 15 mm. The first electrical terminal 104 has a first diameter $d_1$=2.5 mm, and a first length $l_1$=0.2 mm, measured along the longitudinal axis L of the energy source 100, and the second electrical terminal 105 has a second diameter $d_2$=3 mm, and a second length $l_2$=0.2 mm, measured along the longitudinal axis L of the energy source 100. In particular, the first diameter $d_1$ is thus less than the second diameter $d_2$.

The energy source 100 comprises a housing 111, which forms the outside of the main body 101. In the housing 111 there is a voltage source 106 in the form of a circular cylinder. This may be, for example, a CR 2 single cell, known per se, or another round cell known per se. The voltage generated by the voltage source 106 is applied between the second terminal 105 and an inner electrical contact 107, which extend away from the opposite ends of the voltage source 106.

The energy source 100 furthermore has an electrical contact element 108. The latter comprises a holding body 112 in the form, of a circular cylinder, having a holding surface 113 in the form of a circumferential surface of a circular cylinder formed in the circumferential direction. The first terminal 104, likewise in the form of a circular cylinder, is formed on the holding body 112. The contact element 108 thus has a first electrical contact 103, which is formed by the cover surface of the holding body 112 that is opposite the first terminal 104, and which faces toward the inner contact 107, and has a second electrical contact 110, which is formed on the cover surface of the first terminal 104 that is opposite the holding body 112, and which faces away from the inner contact 107. The holding body 112 has a holding-body diameter $D_1$ that is greater than the first diameter $d_1$ of the first terminal 104. The contact element 108 is formed as a single piece from an electrically conductive material such as, for example, gold-plated or nickel-plated brass, such that the first contact 109 and the second contact 110 are electrically connected to each other.

FIG. 1 shows the energy source 100 in a standby position A, in which the contact element 108 is releasably clamped-in on the housing 111, the holding surface 113 being held by mechanical contact with a counter-holding surface 114, in the form of a circumferential surface of a circular cylinder, formed on the housing 111. The first terminal 104 thus extends away in the direction away from the inner contact 107, i.e. away from the main body 101 of the energy source 100.

Formed between the voltage source 106 and the contact element 110 is a first cavity 116, which is delimited partly by the inner contact 107 and by an inner wall 117 in the form of a circumferential surface of a circular cylinder, and an inner wall 118 of the housing 111 in the form of a circular ring. In the standby position A, the first cavity 116 is additionally delimited on the side of the first contact 109 that is opposite the inner contact 107. In the standby position A, however, the contact element 108 does not penetrate into the first cavity 116. However, it would also be possible for the contact element 108, in the standby position A, to penetrate partly into the first cavity 116, but without there being contact between the inner contact 107 and the first contact 109.

Owing to the absence of electrical contact between the inner contact 107 and the first contact 109 of the contact element 103, in the standby position A no voltage is applied between the first terminal 104 and the second terminal 105.

Figure 2:
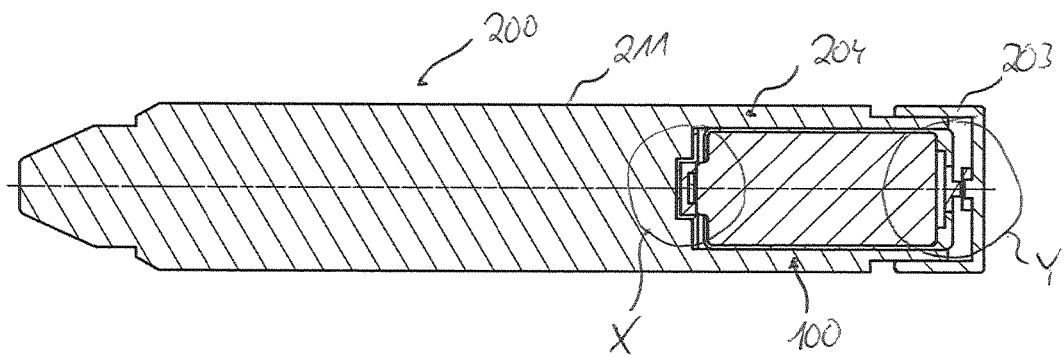
FIG. 2: a lateral sectional view of the first energy source according to the invention accommodated in correct polarity in an electrical screwdriver.

Shown schematically in FIG. 2 is an electrically drivable surgical screwdriver 200. The latter has a housing 211, having a cavity 204 formed therein, accommodated in which is the energy source 100 represented in FIG. 1. Except for its components, described in detail in the following, the screwdriver 200 is represented only schematically. Furthermore, the screwdriver 200 also comprises a cover 203, which serves to hold the energy source 100 inside the cavity 204, and also to close this cavity 204. The screwdriver 200 may, for example, have a length of 17.5 cm and, perpendicular thereto, a diameter of 2.2 cm. The said dimensions allow the screwdriver 200 to be held and operated in one hand. Larger or smaller screwdrivers, which then might only be able to be operated with two hands, are also conceivable. The energy source 100 and the screwdriver 200 form a tool set according to the invention.

Figure 3:
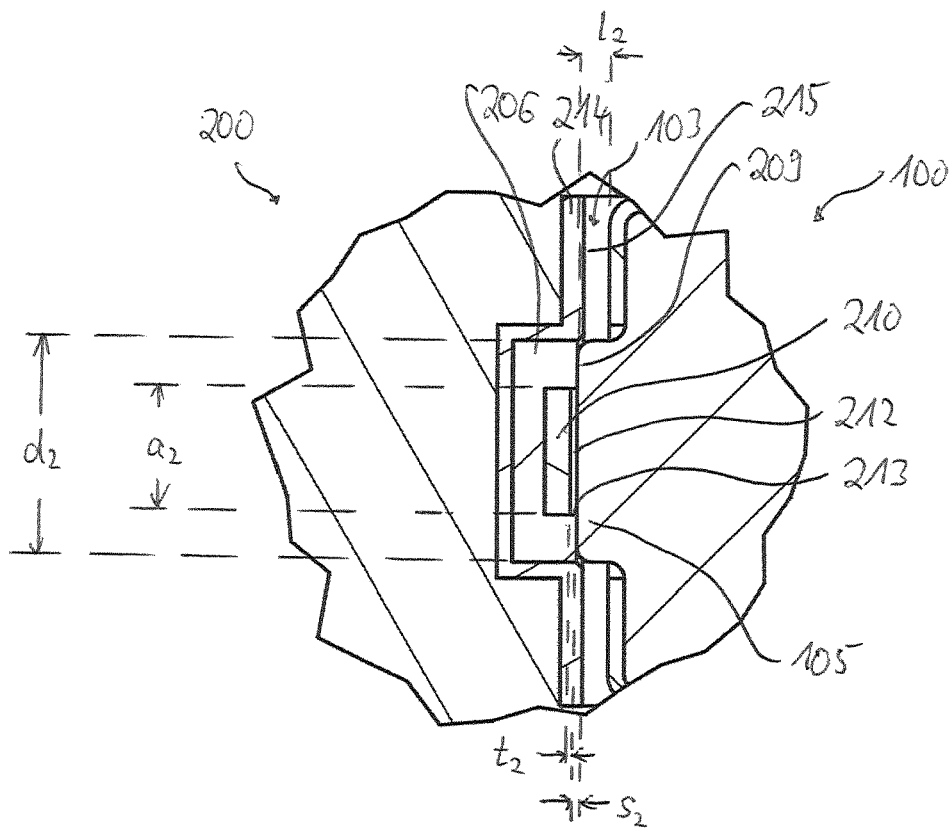
FIG. 3: a detail view of a second terminal of the first energy source according to the invention, and of a second tap-off element of the screwdriver.

FIG. 3 is a detail view of the portion marked by X in FIG. 2. The screwdriver 200 comprises a second tap-off element 206, having an annular second tap-off surface 209 that faces toward the cavity 204. The second tap-off element 206 is arranged in such a manner within a ring insulator 214 having an annular insulator surface 215 that the second tap-off surface 209 is recessed by a distance $s_2$ with respect to the insulator surface 215. The internal diameter of the tap-off surface $a_2$=4 mm is less than the second diameter $d_2$ of the second terminal 105, but greater than the first diameter $d_1$ of the first terminal 104 of the energy source 100. In addition, the distance $s_2$ is less than the length $l_2$ of the second terminal 105. This allows an electrical contact between the second terminal 105 and the second tap-off element 206.

The second tap-off element 206 encompasses, in the manner of a ring, a second insulator 210 and projects over the latter in the longitudinal direction of the screwdriver 200. In this way, a second cavity 212 is formed, which is delimited by an inner wall 213 of the second tap-off element 206 and by the second insulator 210. The second cavity 212 has a second depth $t_2$=0.2 mm along the longitudinal axis L of the energy source 100. The further properties and advantages of this second cavity 212 are to be explained below in connection with FIG. 8.

Figure 4:
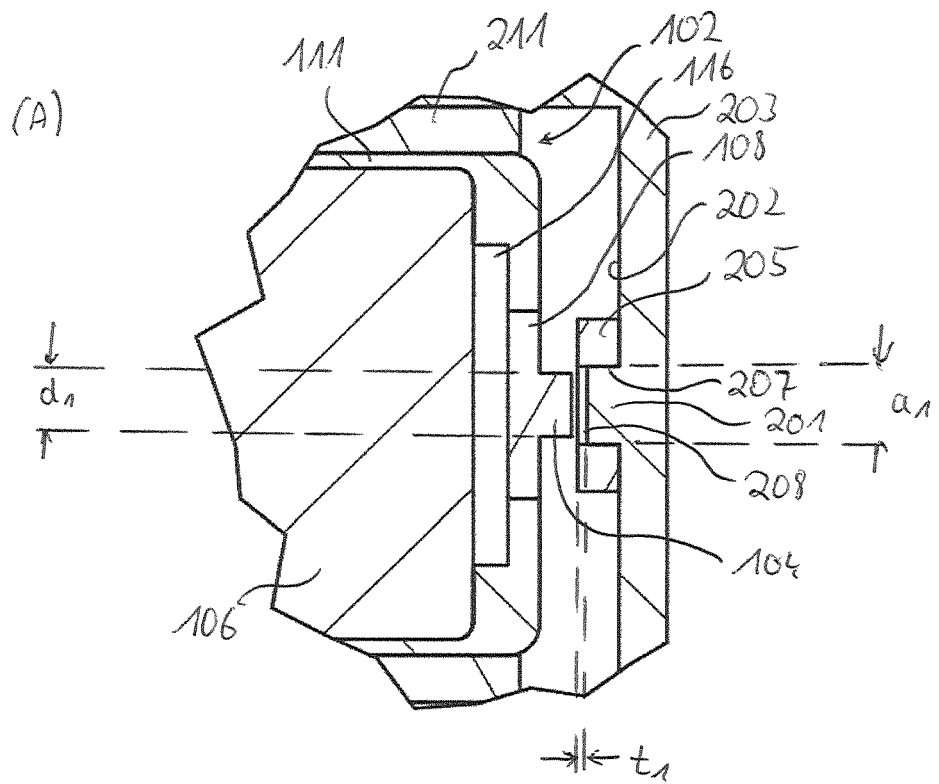
FIG. 4: a detail view of a first terminal of the first energy source according to the invention, and of a first tap-off element of the screwdriver.
Figure 6:
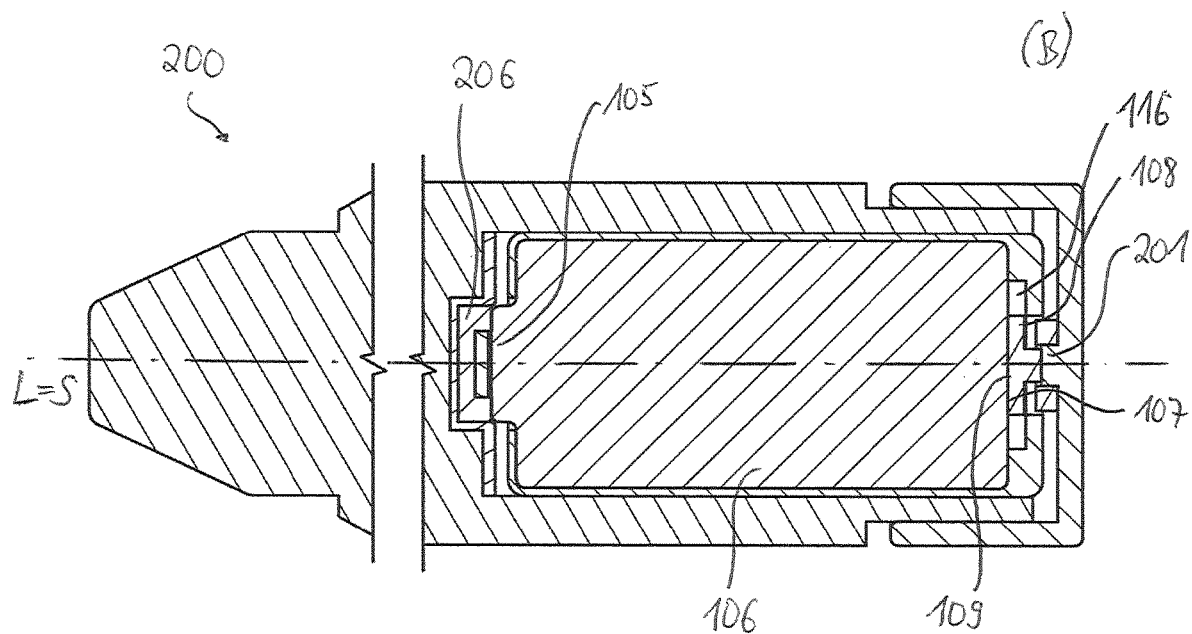
FIG. 6: a detail view of the first terminal of the first energy source according to the invention in the operating position.
Figure 7:
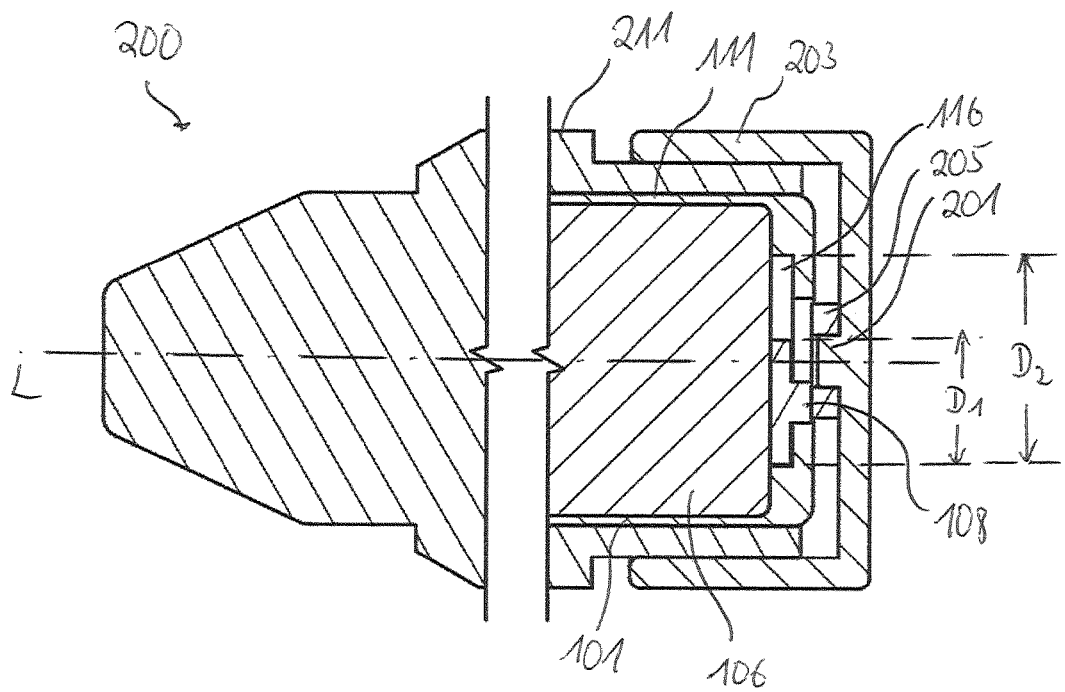
FIG. 7: a detail view of the first terminal of the first energy source according to the invention in the end position.

The detail view in FIG. 4 shows the portion represented by Y in FIG. 2. Arranged on an inner side 202 of the cover 203 are a first tap-off element 201 and a first electrical insulator 205 that encompasses the first tap-off element 201 in the manner of a ring and projects over it in the longitudinal direction of the screwdriver 200. In this way, a first cavity 208 is produced, which is partly delimited by an inner wall 207 of the first insulator 205 and the first tap-off element 201. This first cavity 208 is dimensioned such that the first terminal 104 of the energy source 100 can be accommodated in the first cavity 208 and can be brought into contact with the first tap-off element 201. For this purpose, the internal diameter $a_1$=2.5 mm of the first insulator 205 is greater than the first diameter $d_1$ of the first terminal 104, but less than the second diameter $d_2$ of the second terminal 105 of the energy source. Moreover, the depth $t_1$ of the first cavity 208 is less than the length $l_1$ of the first terminal 104. This contact, however, is produced only in the operating position B represented in FIG. 6 (concerning which, see below).

Figure 5:
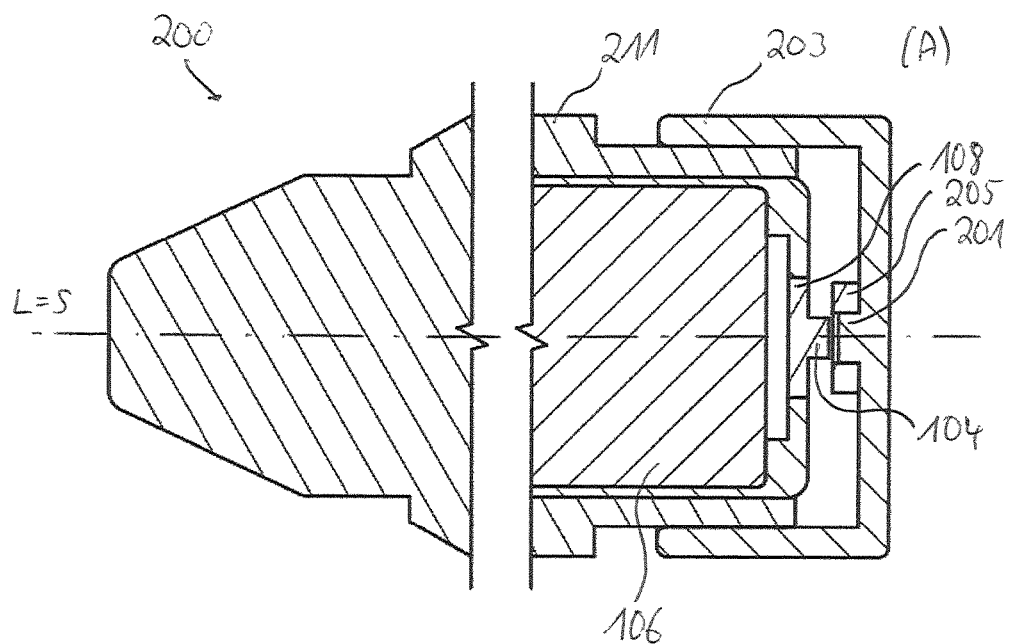
FIG. 5: a detail view of the first terminal of the first energy source according to the invention in the standby position.

FIG. 5 again shows a detail view in the standby position A. As a result of the cover 203 being placed onto the housing 211 of the screwdriver 200, the first terminal 104 of the energy source 100 penetrates into the first cavity 208 and comes into contact with the first tap-off element 201. If the cover 203 is pressed further in the direction of the housing 211, the first tap-off element 201 exerts a force upon the contact element 108, as a result of which the latter is moved from the standby position A shown in FIG. 5 into the operating position B represented in FIG. 6. This movement is effected along an axis of symmetry S of the holding surface 113, which coincides with the longitudinal axis L of the main body 101 of the energy source 100. In other exemplary embodiments, it is also conceivable, more generally, that only one component of the movement goes along the axis of symmetry S of the holding surface 113. The depth $t_1$ of the cavity 208 is dimensioned such that, upon the cover 203 being placed on, the contact element 108, although temporarily loose, is nevertheless always guided in the first insulator 205. Thus, the mechanical guiding can only end when the cover 203 is moved away again from the contact element 108.

In the operating position B, the first contact 109 of the contact element 108 is electrically connected to the inner contact 107. In this way, the first tap-off element 201 is also conductively connected to the inner contact 107. Moreover, the second terminal 105 of the energy source 100 is also in electrical contact with, the second tap-off element 206. Thus, overall, the voltage generated by the voltage source 106 is applied between the first tap-off element 201 and the second tap-off element 206, as a result of which the screwdriver 200 can be driven. In the operating position 3, the contact element 108 is clamped-in, in the direction of the longitudinal axis L, between the inner contact 107 and the first tap-off element 201, and thus cannot slip within the cavity 116.

If the cover 203 is released again from the housing 211, the first tap-off element 201 is also as a result removed from the contact element 108. This results in removal of the clamping action in the direction of the longitudinal axis L. In this end position C, represented in FIG. 8, the contact element 108 is therefore arranged loosely in the cavity 116. As a result, the contact element 108 can slip within the cavity 116, in a plane perpendicular to the longitudinal axis L, in particular as a result of gravity acting thereon. This is possible because the cavity 116, perpendicular to the longitudinal axis L of the main body 101, has a cavity diameter $D_2$ that is greater than the holding-body diameter $D_1$. The loose arrangement is furthermore supported in that the cavity 116, along the longitudinal axis L, is of an extent that is greater than the height of the holding body 112 of the contact element 108, measured along the longitudinal axis L of the main body 101. Alternatively, a spring may be provided, not represented here, which holds the contact element 108 in the end position C, in which it can no longer be brought into electrical contact with the first tap-off element 201; thus, here, the contact element 108 is not arranged loosely in the cavity 116.

The contact element 108 can thus no longer readily be brought into contact with the first tap-off element 201, such that the energy source 100 cannot again be inserted into the screwdriver 200 in such a manner that the latter can be driven by the energy source 100. Moreover, owing to the changed position of the contact element 108, it can be seen from the outside of the energy source 100 that it has already been used in a tool.

Figure 8:
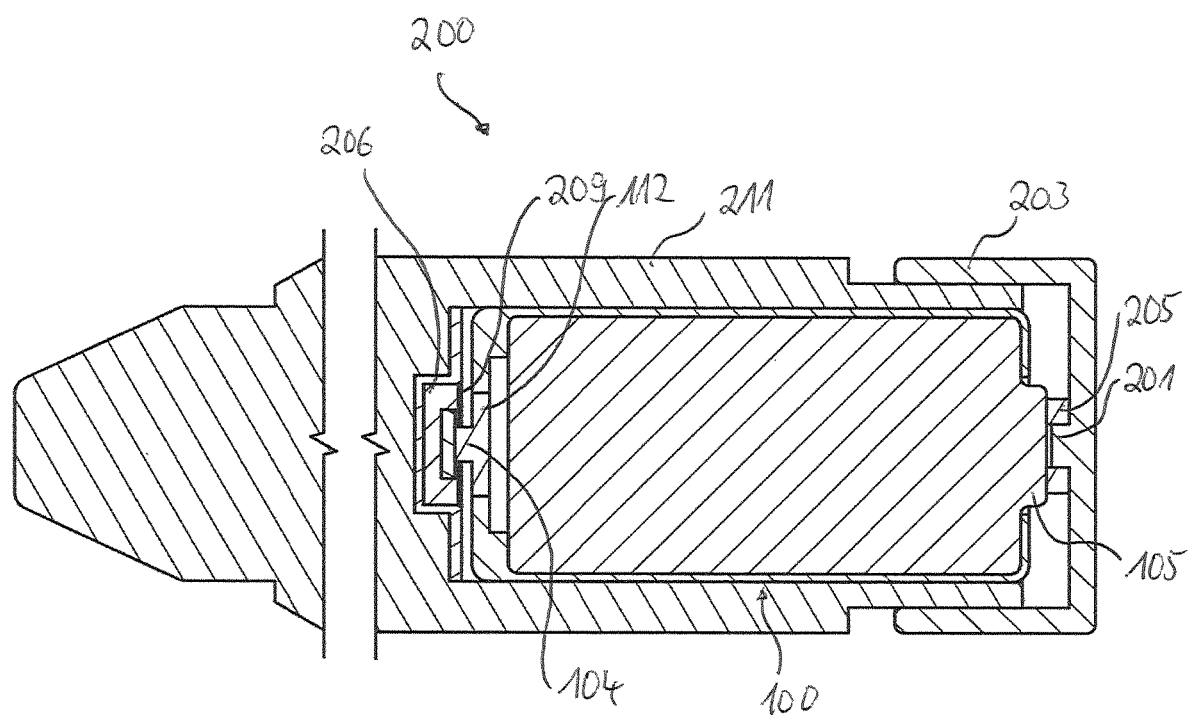
FIG. 8: a lateral sectional, view of the first energy source according to the invention inserted with incorrect polarity.

The same screwdriver 200, having the same energy source 100, is represented in FIG. 8. Here, however, the energy source 100 has been inserted in incorrect polarity; the first terminal 104 is located on the side of the second tap-off element 206, while the second terminal 105 is located on the side of the first tap-off element 201.

On both sides, however, there is no contact between the terminal and the tap-off element; the first terminal 104 has a diameter $d_1$ (see FIG. 1) that is less than the internal diameter as of the second tap-off surface 209 (see FIG. 3). Moreover, the first length $l_1$ of the first terminal 104 (see FIG. 1) is greater than the second depth $t_2$ of the second cavity 212 (see FIG. 3). The first terminal 104 therefore strikes against the second insulator 210 without the holding body 112 in this case being able to come into contact with the second tap-off surface 209. On the other side, the diameter $d_2$ of the second terminal 105 (see FIG. 1) is greater than the internal diameter $a_1$ of the first insulator 205 (see FIG. 4). Therefore the second terminal 105 cannot come into contact with the recessed first tap-off element 201.

The recessing of the second tap-off surface 209 with respect to the insulator surface 215 (see FIG. 3) prevents an energy source, having a terminal that does not, however, extend away from the main body, from being inserted in such a manner that this terminal comes into contact with the second tap-off surface 209. In association with the other statements above, it is established that an energy source that has two terminals, of which, however, at most one extends away from the main body, cannot be brought at all into contact with both tap-off elements 201, 206, in either of the two orientations.

Figure 9:
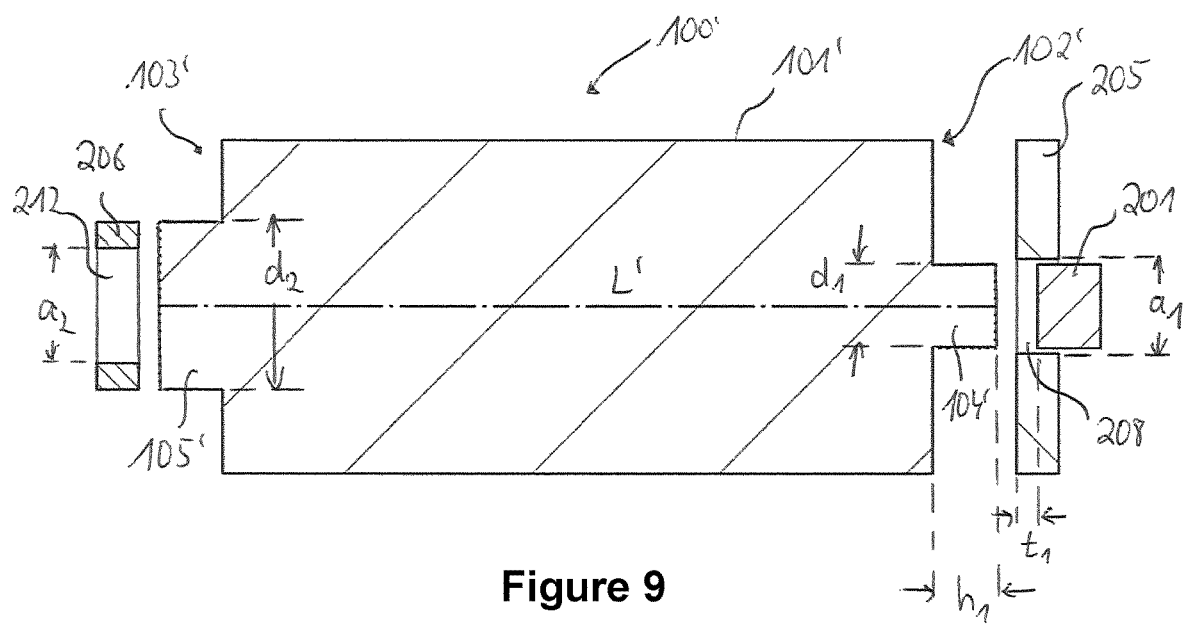
FIG. 9: a schematic: lateral, view of a second energy source according to the invention and two tap-off elements in correct polarity.
Figure 10:
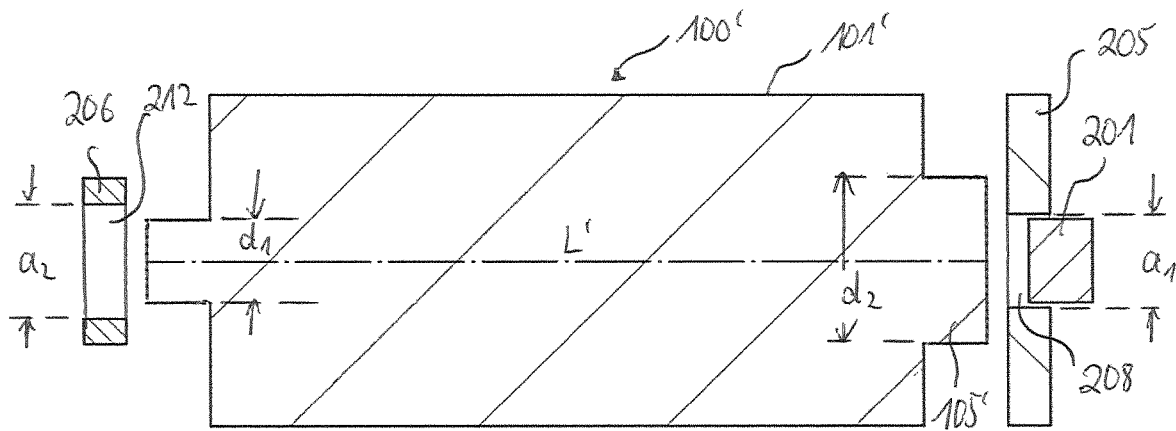
FIG. 10; a schematic lateral view of the second energy source according to the invention and two tap-off elements in incorrect polarity.

A further energy source 100' according to the invention is shown schematically in FIGS. 9 and 10. This energy source also comprises a main body 101', which extends along a longitudinal axis L', and has a first end 102' and a second end 103' that is opposite the first end 102' with respect to the longitudinal axis L'. Extending away from the first end 102' there is a first terminal 104' in the form of a circular cylinder, having a diameter $d_1$, and extending away from the second end 103' there is a second terminal 105', having a second diameter $d_2$, which is greater than the first diameter $d_1$. Unlike the first exemplary embodiment represented in FIGS. 1 to 8, the energy source 100' does not comprise a movable contact element. Instead, the first terminal 104' is arranged in an immovable manner on the main body 101'.

Furthermore, represented schematically in FIGS. 9 and 10 are a first tap-off element 201 in the form of a circular cylinder, a first insulator 205, and an annular second tap-off element 206 that encompasses a second cavity 212. The first insulator 205 encompasses the first tap-off element 201 in the manner of a ring, and projects over the latter in the direction of the second tap-off element 206. The first insulator 205 has an internal diameter a that is greater than the diameter $d_1$ of the first terminal 104', but less than the diameter $d_2$ of the second terminal 105'. Furthermore, the length $l_1$ of the first terminal 104', measured along the longitudinal axis L', is greater than the first depth $t_1$ of a first cavity 208, measured in this direction, which cavity is delimited by the first tap-off element 201 and an inner wall 207 of the first insulator 205. The internal diameter $a_2$ of the second tap-off element 206 is greater than the internal diameter $a_1$ of the first insulator 105, and consequently likewise greater than the diameter $d_1$ of the first terminal 104', but less than the diameter of the second terminal 105'. Thus, overall, $d_1 < a_1 < a_2 < d_2$.

In FIG. 9, the energy source 100' is oriented in correct polarity. If the energy source 100' and the first insulator 205 are moved, together with the first tap-off element 201, in the direction of the second tap-off element 206, the first terminal 104' penetrates into the cavity 208, because of the dimensions described above, such that it comes into contact with the first tap-off element 201, and the second terminal 105f bears against the second tap-off element 206. Thus, in this way, the voltage generated by the energy source 100' is applied between the two tap-off elements 201 and 206.

In FIG. 10, the energy source 100f is oriented in incorrect polarity. Here, the first terminal 104' penetrates into the second cavity 212 formed in the second tap-off element 206. Since, however, the diameter $d_1$ of the first terminal is less than the internal diameter $a_2$, no electrical contact is produced here. Moreover, since the second diameter $d_2$ is greater than the internal diameter $a_1$ of the first insulator 205, the second terminal 105' cannot come into contact with the first tap-off element 201.

An energy source (not according to the invention) having two terminals of identical diameter $d_1 = d_2$ would not ensure such polarity reversal protection: this is because, in that case, either the two identical diameters $d_1 = d_2$ of the terminals would both be less than the greater internal diameter $a_2$, such that neither of the two terminals could come into contact with the second tap-off element 206, or, alternatively, the two identical diameters $d_1 = d_2$ of the terminals would be at least as great as the greater internal diameter $a_2$, i.e. greater than the lesser internal diameter $a_1$, in which case, then, however, neither of the two terminals could come into contact with the first tap-off element 201, since they would both strike against the first insulator 205. Moreover, for the user, such an energy source would be difficult to insert correctly, since the two terminals do not differ visually.

Shown schematically in FIGS. 11a to 11i are a plurality of further energy sources 100', of which only the first, terminal 104' is visible in each case. The first terminals 104' of all energy sources 100' represented in FIGS. 11a to 11i have the same diameter $d_1'$, as understood according to the present invention. FIGS. 11a to 11i each, show a notional hollow cylinder 119', the longitudinal axis of which coincides with the longitudinal axis of the main body 101f. Represented in each case is the smallest such notional hollow cylinder 119' in which the first terminal 104' can be fully accommodated. According to the definition used here, the diameter $d_1'$ of the first terminal 104' is the diameter of this minimum notional hollow cylinder 119'.

Figure 11A:
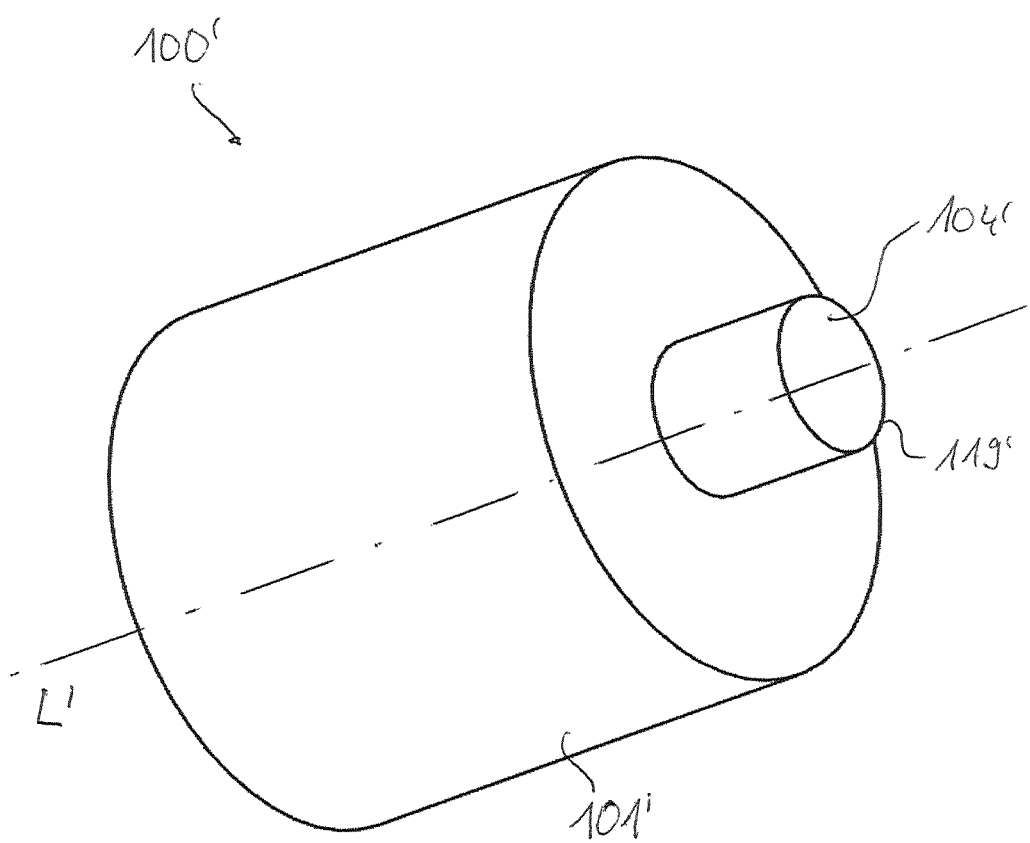
Figures 11B, 11C:
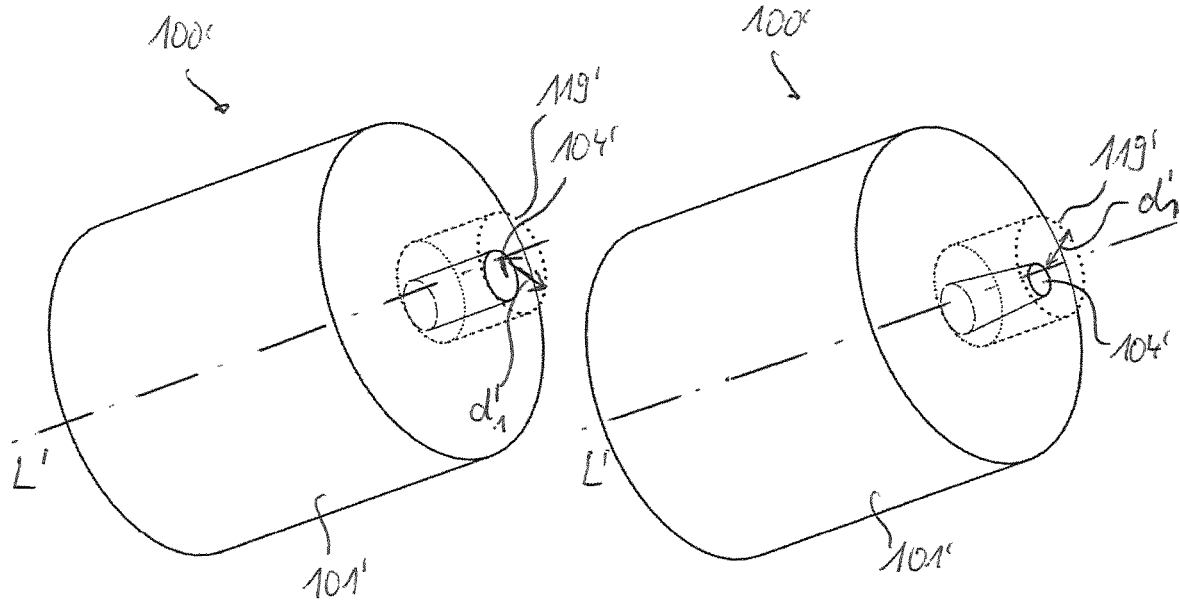
Figures 11D, 11E:
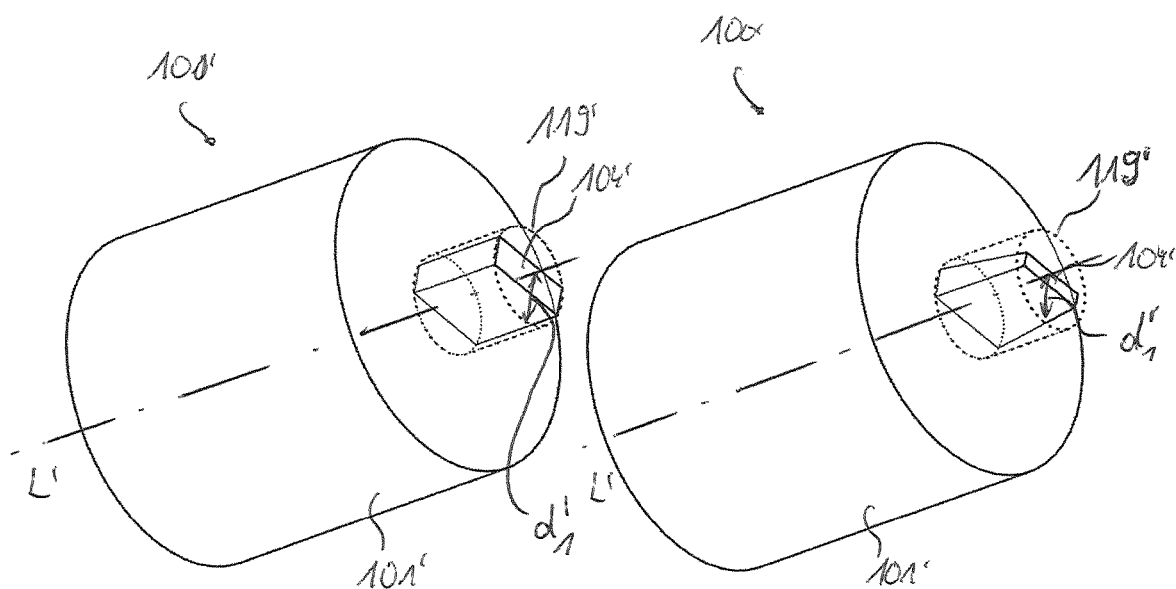

In detail, in FIG. 11a the first terminal 104d is in the form of a circular cylinder and arranged along the longitudinal, axis L' of the main body 101'. Here, the first terminal 104' thus coincides with the notional hollow cylinder 119f, and is identical to that represented in FIGS. 9 and 10. The first terminal 104f according to FIG. 11b has the form, of a circular cylinder, of which, however, the axis of symmetry has been displaced eccentrically with respect to the longitudinal axis L' of the main body 101'. The first terminal 104f according to FIG. 11c is likewise arranged eccentrically, but has the form of a circular truncated cone. The first terminal 104' illustrated in FIG. 11d is in the form of a rectangular parallelepiped, if first terminal 101' in the form of a truncated cone, having a rectangular, but not square, base, is represented in FIG. 11e. FIG. 11f shows a first terminal 104' in the form of an eccentric circular cone. The embodiment represented in FIG. 11g comprises a first terminal 104' that is in the form of a helix and that, for example, may additionally be realized as a spring. The exemplary embodiment according to FIG. 11g comprises in total five first terminals 104f, which are each realized in the form of a rod and arranged in the circumferential direction around the longitudinal axis L'. Finally, FIG. 11h shows a first terminal 104' in the form of a hollow cylinder having a central bore 120f. Clearly, any combinations of the above-mentioned exemplary embodiments are also conceivable.

The invention claimed is:

1. An electrical energy source for an electrically drivable tool, comprising:
   a housing,
   at least one voltage source, arranged in the housing, for generating an electrical voltage,
   at least one second terminal, and
   at least one inner electrical contact;
   wherein the voltage generated by the voltage source is applied or can be applied between the second terminal and the inner electrical contact;
   wherein the electrical energy source comprises
   at least one electrical contact element having a first electrical contact and a second electrical contact that are electrically connected to each other,
   the at least one electrical contact element comprises a first terminal, which comprises the second electrical contact;
   the at least one electrical contact element is in a standby position, in which it is releasably connected, directly or indirectly, to the housing, and in which neither the first electrical contact nor the second electrical contact is electrically connected to the inner electrical contact;
   by action of a force that can be exerted by a first tap-off element of the tool, the at least one electrical contact element can be moved from the standby position into an operating position in which the first electrical contact is electrically connected to the inner electrical contact such that the voltage generated by the voltage source is applied between the second terminal and the first tap-off element;
   after the first tap-off element is removed for a first time, the at least one electrical contact element moves from the operating position into an end position in which the at least one electrical contact element can no longer be brought into electrical contact with the first tap-off element such that the voltage generated by the voltage source can no longer be applied between the second terminal and the first tap-off element.

2. The energy source as claimed in claim 1, wherein in the standby position the at least one electrical contact element may be clamped in, adhesive-bonded in, pressed in or welded in on the housing, or connected to the housing via at least one predetermined breaking point.

3. The energy source according to claim 1, wherein the at least one electrical contact element has a holding surface, and the housing has a counter-holding surface, and the at least one electrical contact element can be held in the standby position by mechanical contact of the holding surface with the counter-holding surface.

4. The energy source according to claim 3, wherein the at least one electrical contact element is movable along a longitudinal axis, from the standby position into the operating position.

5. The energy source according to claim 4, wherein a longitudinal axis of the holding surface coincides with a longitudinal axis of a main body.

6. The energy source according to claim 1, further comprising at least one cavity, in which the at least one electrical contact element is loosely arranged in the end position.

7. The energy source according to claim 6, wherein the cavity is realized substantially in a form of a circular cylinder and has a cavity diameter, perpendicular to the longitudinal axis of the main body, wherein the cavity diameter is greater than a holding-body diameter.

8. A tool set, comprising:
   at least one electrically drivable tool,
   at least one electrical energy source according to claim 1, by which the tool is electrically drivable.

9. The tool set according to claim 8, wherein the tool has said first tap-off element, which is realized and arranged in such a manner that the at least one electrical contact element of the energy source is moved from the standby position into the operating position by action of a force that can be exerted by the first tap-off element.

10. The tool set according to claim 8, wherein the electrically drivable tool is an electrically drivable surgical tool.

11. The tool set according to claim 8, wherein the electrically drivable tool is an electrically driveable surgical screwdriver.

12. A method for inserting an energy source according to claim 1 into an electrically drivable tool, comprising a step in which, by action of a force by the first tap-off element of the tool, the contact element of the energy source is moved from the standby position into the operating position.

* * * * *